# United States Patent [19]

Masia et al.

[11] Patent Number: 5,382,909
[45] Date of Patent: * Jan. 17, 1995

[54] METHOD FOR DETECTING AND OBTAINING INFORMATION ABOUT CHANGES IN VARIABLES

[75] Inventors: Michael Masia, Redwood City; James P. Reed, San Francisco; Robert S. Wasley, San Carlos; Larry R. Reeder, San Jose; Peter L. Brooks, Los Altos; Thomas W. Tolles, San Francisco; Louis M. Frank, Sunnyvale; Mauro Bonomi, Palo Alto; Ray F. Stewart, Redwood City; John Lahlough, San Jose; Laurence Welsh, Palo Alto, all of Calif.

[73] Assignee: Raychem Corporation, Menlo Park, Calif.

[ * ] Notice: The portion of the term of this patent subsequent to May 15, 2007 has been disclaimed.

[21] Appl. No.: 100,710

[22] Filed: Jul. 30, 1993

Related U.S. Application Data

[63] Continuation of Ser. No. 698,012, May 9, 1991, Pat. No. 5,235,286, which is a continuation of Ser. No. 372,179, Jun. 27, 1989, Pat. No. 5,015,958, which is a continuation of Ser. No. 306,237, Feb. 2, 1989, abandoned, which is a continuation of Ser. No. 832,562, Feb. 20, 1986, abandoned, which is a continuation-in-part of Ser. No. 599,047, Apr. 11, 1984, abandoned, which is a continuation-in-part of Ser. No. 509,897, Jun. 30, 1983, abandoned, said Ser. No. 832,562, is a continuation-in-part of Ser. No. 599,048, Apr. 11, 1984, abandoned, which is a continuation-in-part of Ser. No. 509,897, Apr. 11, 1984, said Ser. No. 832,562, is a continuation-in-part of Ser. No. 556,740, Nov. 30, 1983, abandoned, said Ser. No. 832,562, is a continuation-in-part of Ser. No. 556,829, Dec. 1, 1983, abandoned, which is a continuation-in-part of Ser. No. 556,740, Aug. 20, 1984, said Ser. No. 832,562, is a continuation-in-part of Ser. No. 618,106, Jun. 7, 1984, abandoned, said Ser. No. 832,562, is a continuation-in-part of Ser. No. 618,109, Jun. 7, 1984, abandoned, said Ser. No. 832,562, is a continuation-in-part of Ser. No. 618,108, Jun. 7, 1984, which is a continuation-in-part of Ser. No. 603,485, Apr. 24, 1984, abandoned, said Ser. No. 832,562, is a continuation-in-part of Ser. No. 603,484, Apr. 24, 1984, abandoned, said Ser. No. 832,562, is a continuation-in-part of Ser. No. 691,291, Jan. 14, 1985, abandoned, said Ser. No. 832,562, is a continuation-in-part of Ser. No. 809,321, Dec. 17, 1985, abandoned, which is a continuation-in-part of Ser. No. 691,291, Dec. 17, 1985, said Ser. No. 832,562, is a continuation-in-part of Ser. No. 744,170, Jun. 12, 1985, abandoned, said Ser. No. 832,562, is a continuation-in-part of Ser. No. 787,278, Oct. 15, 1985, abandoned.

[51] Int. Cl.$^6$ .................. G01R 31/08; H01B 7/32
[52] U.S. Cl. .......................... 324/522; 324/525; 324/526; 174/11 R; 340/537
[58] Field of Search ............... 324/522, 509, 525, 526, 324/512, 523, 539, 551, 691; 379/26; 346/602–605, 637; 174/11 R

[56] References Cited

U.S. PATENT DOCUMENTS 1,084,910 1/1914 Stephenson .
1,648,197 11/1927 Roadhouse .

(List continued on next page.)

FOREIGN PATENT DOCUMENTS 58704 4/1913 Austria .
719311 10/1965 Canada ............................ 200/61.04

(List continued on next page.)

OTHER PUBLICATIONS

"WaterSentry LeakSentry Distributed Alarm and Locator Systems", Raychem Corporation, Jan. 1984.

(List continued on next page.)

Primary Examiner—Maura K. Regan
Attorney, Agent, or Firm—Timothy H. P. Richardson; Herbert G. Burkard

[57] ABSTRACT

Detection of liquid leaks and other changes in variables is disclosed. The event causes two elongate conductors to become electrically connected at a location which is determined by the event, thus creating a system in which the connection point can be located by measuring the potential drop from one end of one of the conductors (called the locating member) to the connection point. The system comprises a balancing component so that its sensitivity is not dependent on the location of the event along an elongate path. A fixed current flows through the connection, so that the result is independent (Abstract continued on next page.)

ABSTRACT of the resistance of the connection. The locating member can be a continuous resistive wire, coated with a conductive polymer; such a locating member can form part of a sensor cable in which the elongate components of the circuit are in a wrapped configuration. Alternatively the locating member comprises a plurality of discrete resistors. The system is arranged so that only connections within a certain range of resistance will activate the system. The voltage drop is calculated by comparing it to the voltage drop over a resistor of known size. Particular event-sensitive connection means are employed for the detection of hydrocarbons.

13 Claims, 4 Drawing Sheets

U.S. PATENT DOCUMENTS

| | | | |
|---|---|---|---|
| 1,772,232 | 8/1930 | Van Guilder . | |
| 1,786,843 | 12/1930 | Hedeby | 200/193 |
| 2,004,569 | 6/1935 | Davis, Jr. | 175/183 |
| 2,360,434 | 10/1944 | Manning | 200/61.05 |
| 2,432,367 | 12/1947 | Andresen | 200/52 |
| 2,563,341 | 8/1951 | Kettering | 200/61.05 |
| 2,581,213 | 1/1952 | Spooner | 177/311 |
| 2,691,134 | 10/1954 | Ford | 324/65 |
| 2,716,229 | 8/1955 | Wehrmann | 340/605 |
| 2,741,591 | 4/1956 | Dewey, II et al. | 204/180 |
| 2,759,175 | 8/1956 | Spalding | 340/242 |
| 2,790,146 | 4/1957 | Livingston | 324/140 |
| 2,841,765 | 7/1958 | Harrold | 324/62 |
| 2,879,471 | 3/1959 | Erath | 324/62 |
| 2,881,392 | 4/1959 | Heinz | 324/98 |
| 2,930,232 | 3/1960 | Spears | 73/304 R |
| 2,976,486 | 3/1961 | Gilbert | 324/64 |
| 3,033,916 | 5/1962 | Scofield | 174/117 |
| 3,045,198 | 7/1962 | Dolan et al. | 338/13 |
| 3,098,116 | 7/1963 | Jore | 200/61.04 |
| 3,127,485 | 3/1964 | Vitolo | 200/61.05 |
| 3,200,388 | 8/1965 | Uhlig | 340/242 |
| 3,248,646 | 4/1966 | Brazee | 324/52 |
| 3,254,334 | 5/1966 | Mitchell | 340/514 |
| 3,304,612 | 2/1967 | Proctor | 178/18 |
| 3,365,661 | 1/1968 | Zimmerman | 324/52 |
| 3,382,493 | 5/1968 | Loper, Jr. et al. | 340/244 |
| 3,383,863 | 5/1968 | Berry | 61/1 |
| 3,427,414 | 2/1969 | Sheldahl | 200/61.04 |
| 3,465,109 | 9/1969 | Williams | 200/61.04 |
| 3,470,340 | 9/1969 | Hakka | 200/61.04 |
| 3,520,476 | 7/1970 | Schmid | 200/61.04 |
| 3,550,120 | 12/1970 | Kompelien | 340/409 |
| 3,564,526 | 2/1971 | Butts | 200/61.04 |
| 3,588,776 | 6/1971 | Horwinski | 340/508 |
| 3,600,674 | 8/1971 | Brea | 324/52 |
| 3,662,367 | 5/1972 | Deveau | 174/11 R |
| 3,702,473 | 11/1972 | Fink | 340/511 |
| 3,706,927 | 12/1972 | Jedvall | 324/52 |
| 3,721,898 | 3/1973 | Dragoumis et al. | 324/65 |
| 3,800,216 | 3/1974 | Hamilton | 324/52 |
| 3,800,217 | 3/1974 | Lowrence | 324/54 |
| 3,812,420 | 5/1974 | Gunter | 324/52 |
| 3,849,723 | 11/1974 | Allen | 324/446 |
| 3,852,995 | 12/1974 | Duncanson | 73/40 |
| 3,866,202 | 2/1975 | Reiss et al. | 340/274 |
| 3,875,331 | 4/1975 | Hasenbalg | 178/18 |
| 3,885,097 | 5/1975 | Pobgee | 178/18 |
| 3,970,863 | 7/1976 | Kishikawa et al. | 307/116 |
| 3,981,181 | 12/1976 | Ochiai | 73/40.5 |
| 3,991,413 | 11/1976 | Berger | 340/537 |
| 4,013,924 | 3/1977 | Christensen | 174/11 R |
| 4,023,412 | 5/1977 | Luke et al. | 73/40.5 R |

(List continued on next page.)

FOREIGN PATENT DOCUMENTS

| | | | |
|---|---|---|---|
| 028142 | 5/1981 | European Pat. Off. . | |
| 056283 | 1/1982 | European Pat. Off. . | |
| 067679 | 12/1982 | European Pat. Off. . | |
| 068767 | 1/1983 | European Pat. Off. . | |
| 087307 | 8/1983 | European Pat. Off. . | |
| 1260189 | 3/1961 | France . | |
| 684427 | 11/1939 | Germany | 73/40.5 R |
| 899978 | 7/1949 | Germany | 324/526 |
| 1210057 | 2/1966 | Germany | 200/61.04 |
| 1297682 | 6/1969 | Germany . | |
| 2135214 | 2/1973 | Germany | 333/81 R |
| 2413996 | 12/1974 | Germany . | |
| 2455007 | 5/1976 | Germany . | |
| 2517769 | 10/1976 | Germany . | |

(List continued on next page.)

OTHER PUBLICATIONS

Stubbings, "Electrical Review", Dec. 28, 1945, p. 947
Data Aquisition Handbook, 1982.

U.S. PATENT DOCUMENTS

| Number | Date | Name | Class |
|---|---|---|---|
| 4,029,889 | 6/1977 | Mizuochi | 174/11 |
| 4,052,901 | 10/1977 | Bjork | 73/304 R |
| 4,095,174 | 6/1978 | Ishido | 324/52 |
| 4,125,822 | 11/1978 | Perren et al. | 338/34 |
| 4,129,030 | 12/1978 | Dolan | 73/23 |
| 4,184,143 | 1/1980 | Stafford | 367/13 |
| 4,193,068 | 3/1980 | Ziccardi | 200/61.04 |
| 4,206,632 | 6/1980 | Suzuki | 340/605 |
| 4,224,595 | 9/1980 | Dolan | 338/34 |
| 4,237,721 | 12/1980 | Dolan | 73/23 |
| 4,246,575 | 1/1981 | Purtell | 340/605 |
| 4,263,115 | 4/1981 | Kessler | 204/418 |
| 4,278,931 | 7/1981 | Huggins | 324/52 |
| 4,288,653 | 9/1981 | Blom et al. | 174/47 |
| 4,288,654 | 9/1981 | Blom et al. | 174/47 |
| 4,297,686 | 10/1981 | Tom | 340/604 |
| 4,298,969 | 11/1981 | Rickenbacker | 367/13 |
| 4,305,321 | 12/1981 | Cohn | 84/1.24 |
| 4,307,606 | 12/1981 | Johnson | 73/295 |
| 4,319,078 | 3/1982 | Yokoo | 178/18 |
| 4,319,184 | 3/1982 | Kowalczyk | 333/81 R |
| 4,319,232 | 3/1982 | Westphal et al. | 340/604 |
| 4,359,721 | 11/1982 | Galvin et al. | 340/525 |
| 4,369,436 | 1/1983 | Lautzenheiser | 340/510 |
| 4,374,379 | 2/1983 | Dennison, Jr. | 200/61.05 |
| 4,386,231 | 5/1983 | Vokey | 174/115 |
| 4,400,663 | 8/1983 | May | 324/525 |
| 4,404,516 | 9/1983 | Johnson | 340/605 |
| 4,414,441 | 11/1983 | Perry et al. | 200/61.04 |
| 4,423,410 | 12/1983 | Galvin et al. | 340/525 |
| 4,424,479 | 1/1984 | Brown | 324/52 |
| 4,445,012 | 4/1984 | Blackburn et al. | 200/61.04 |
| 4,446,421 | 5/1984 | Berde | 324/52 |
| 4,449,098 | 5/1984 | Nakamura et al. | 138/104 |
| 4,467,286 | 8/1984 | Stitt | 333/81 R |
| 4,468,306 | 8/1984 | Freeman et al. | 204/180 |
| 4,468,607 | 8/1984 | Tanaka | 333/81 R |
| 4,503,526 | 3/1985 | Beauducel | 367/13 |
| 4,537,668 | 8/1985 | Gaussens et al. | 204/159.17 |
| 4,553,432 | 11/1985 | Barlian | 338/35 |
| 4,563,674 | 1/1986 | Kobayashi | 340/605 |
| 4,570,477 | 2/1986 | Sugibuchi | 174/11 R |
| 4,571,292 | 2/1986 | Liu | 204/412 |
| 4,594,638 | 1/1986 | Suzuki | 174/11 R |
| 4,631,952 | 12/1986 | Donaghey | 338/34 |
| 4,677,371 | 6/1987 | Imaizumi | 174/11 R |
| 5,015,958 | 5/1991 | Masia et al. | 324/522 |
| 5,235,286 | 8/1993 | Masia et al. | 324/522 |

FOREIGN PATENT DOCUMENTS

| | | | |
|---|---|---|---|
| 2911703 | 3/1979 | Germany . | |
| 2807084 | 8/1979 | Germany . | |
| 3011500 | 10/1981 | Germany . | |
| 3225742 | 2/1983 | Germany . | |
| 3140804 | 4/1983 | Germany . | |
| 3239133 | 6/1983 | Germany . | |
| 3209560 | 9/1983 | Germany . | |
| 3441924 | 5/1985 | Germany | 73/40.5 R |
| 566133A | 1/1981 | Japan . | |
| 133370 | 8/1982 | Japan . | |
| 94185 | 5/1984 | Japan | 178/18 |
| 112266 | 6/1985 | Japan . | |
| 182339 | 7/1922 | United Kingdom . | |
| 547461 | 8/1942 | United Kingdom . | |
| 561523 | 5/1944 | United Kingdom . | |
| 591822 | 8/1947 | United Kingdom | 73/40.5 R |
| 646392 | 11/1950 | United Kingdom . | |
| 919517 | 2/1963 | United Kingdom . | |
| 939049 | 10/1963 | United Kingdom | 200/61.04 |
| 1178231 | 1/1970 | United Kingdom . | |
| 1352124 | 5/1974 | United Kingdom . | |
| 1355176 | 6/1974 | United Kingdom | 73/40.5 R |
| 1401146 | 7/1975 | United Kingdom . | |
| 1470503 | 4/1977 | United Kingdom . | |
| 1481850 | 8/1977 | United Kingdom . | |
| 1550550 | 8/1979 | United Kingdom . | |
| 2043974 | 10/1980 | United Kingdom . | |
| 2077471 | 12/1981 | United Kingdom . | |
| 2091880 | 8/1982 | United Kingdom . | |
| 678646 | 8/1979 | U.S.S.R. . | |
| WO8301138 | 3/1983 | WIPO . | |

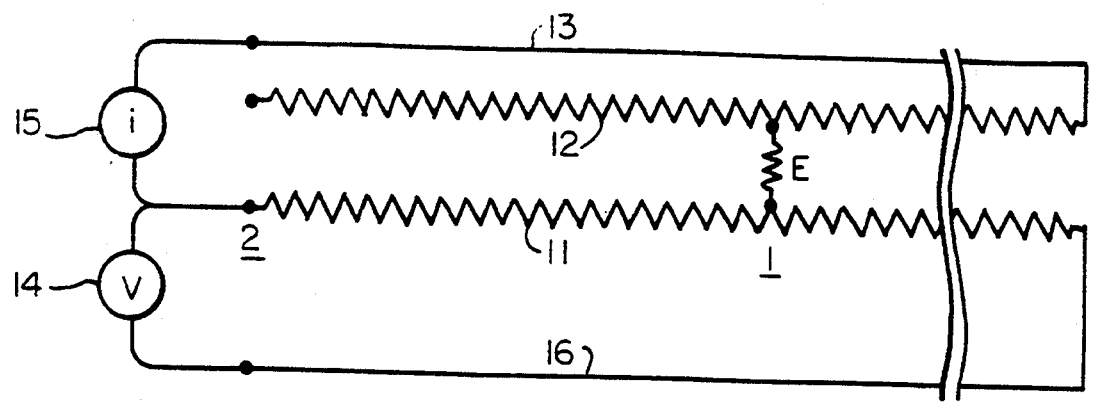
FIG__1
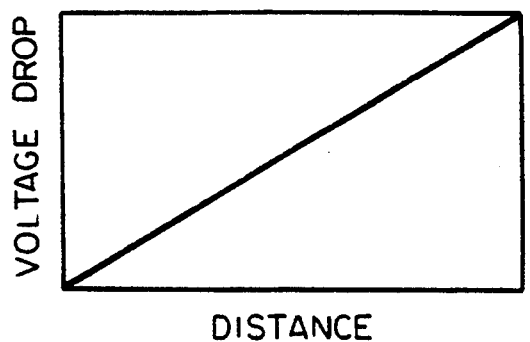
FIG__2
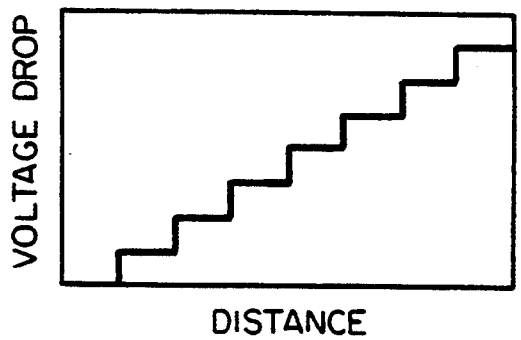
FIG__3
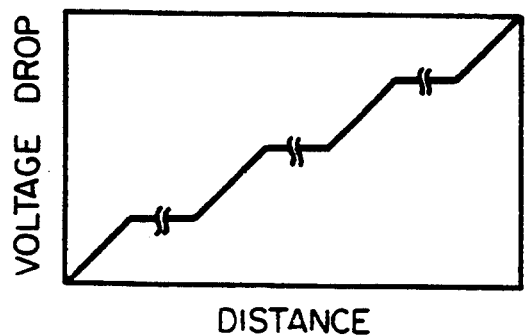
FIG__4

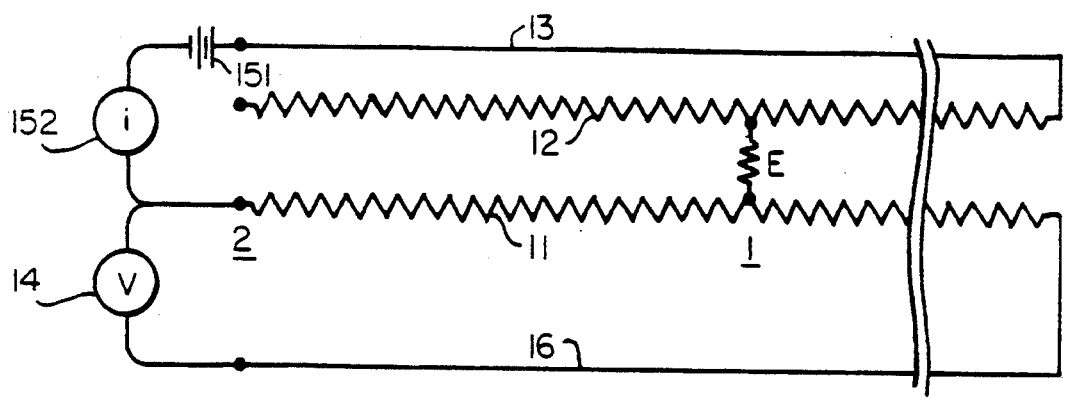
*FIG_5*
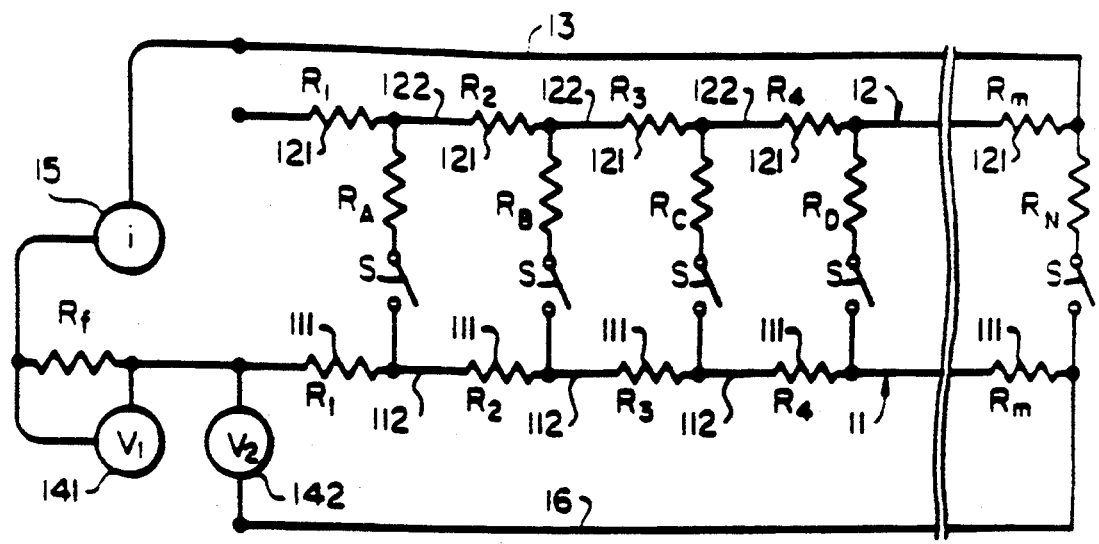
*FIG_6*
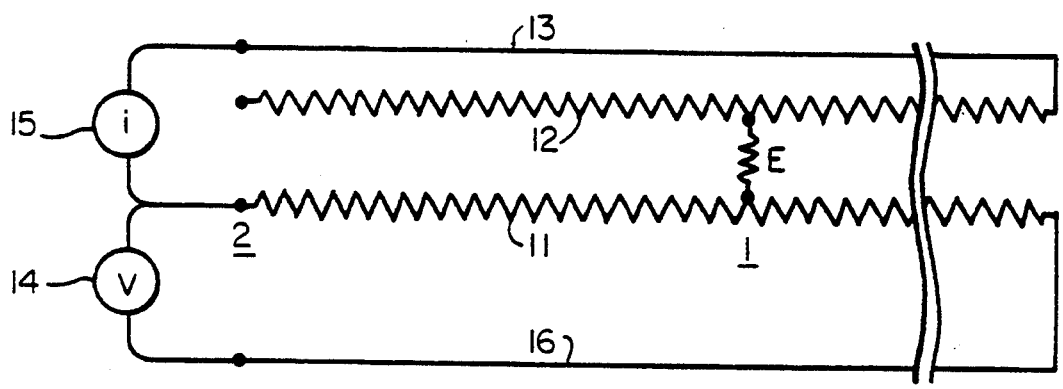
*FIG_7*

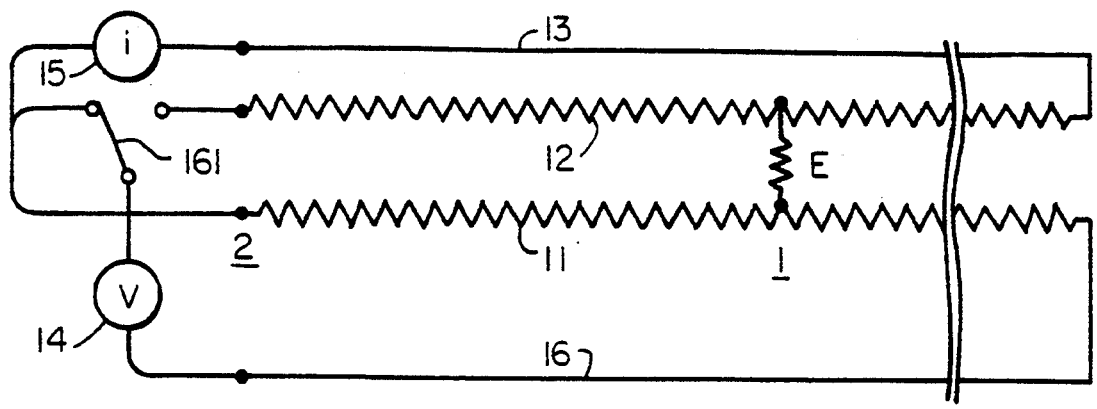
FIG_8
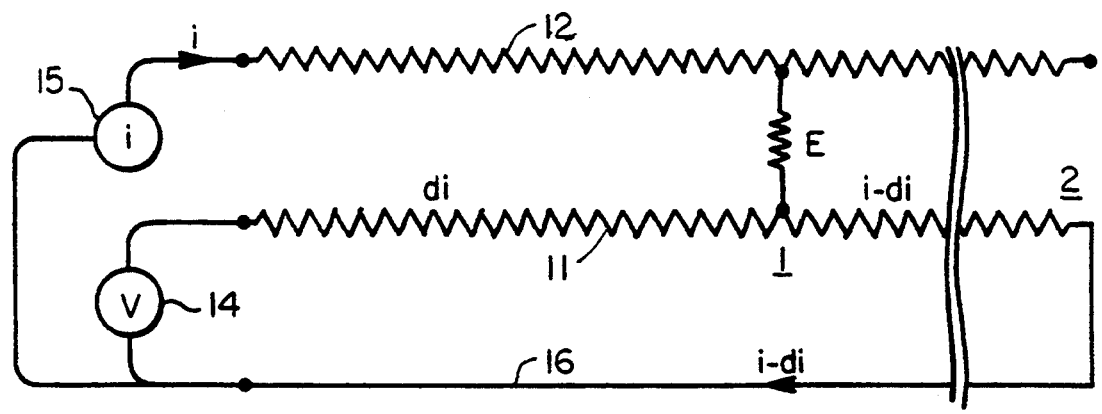
FIG_9
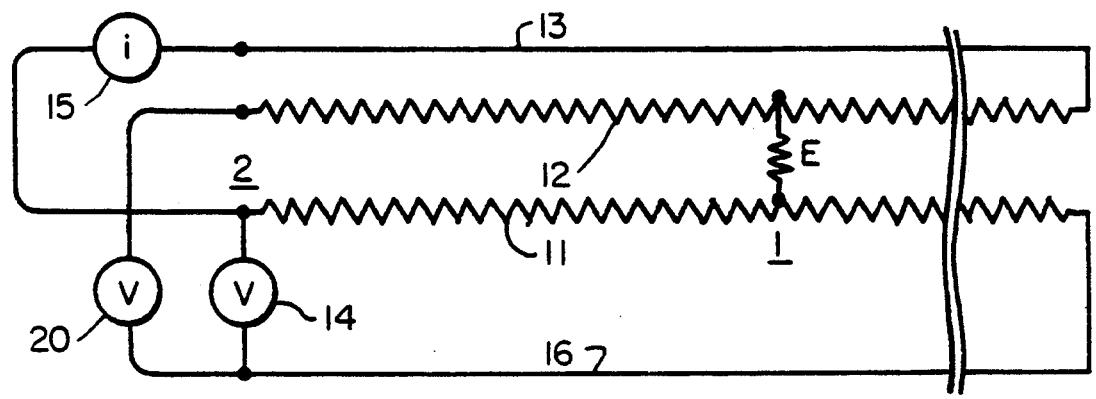
FIG_10

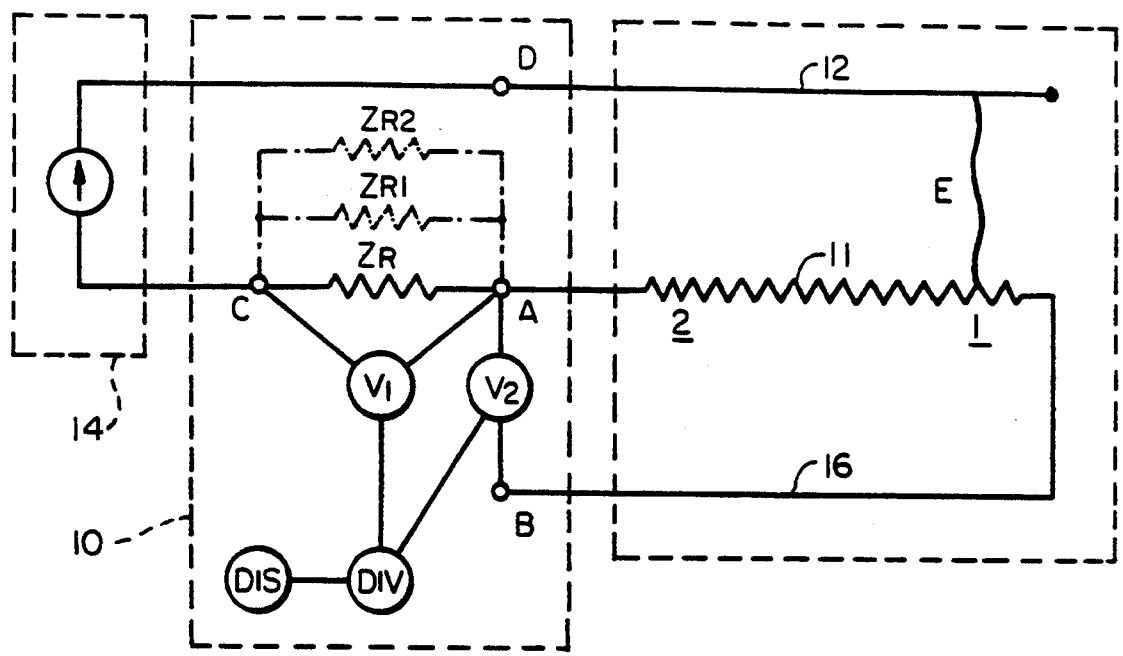
FIG_11

METHOD FOR DETECTING AND OBTAINING INFORMATION ABOUT CHANGES IN VARIABLES

CROSS-REFERENCE TO RELATED APPLICATIONS

This application is a continuation of copending commonly assigned Application Ser. No. 07/698,012 filed May 9, 1991, now U.S. Pat. No. 5,235,286, which is a continuation of Ser. No. 07/372,179 filed Jun. 27, 1989, now U.S. Pat. No. 5,015,958, which is a continuation of Ser. No. 07/306,237 filed Feb. 2, 1989, now abandoned, which is a continuation of Ser. No. 06/832,562 filed Feb. 20, 1986, now abandoned. Ser. No. 06/832,562 is a continuation-in-part of each of the following commonly assigned applications:

(1) Ser. No. 599,047 filed Apr. 11, 1984, by Masia and Reed, (MP0869-US2) now abandoned, which is a continuation-in-part of Ser. No. 509,897, filed Jun. 30, 1983, by Masia and Reed (MP0869-US1) now abandoned;

(2) Ser. No. 599,048, filed Apr. 11, 1984, by Masia and Reed (MP0869-US3) now abandoned, which is also a continuation-in-part of Ser. No. 509,897, filed Jun. 30, 1983, by Masia and Reed (MP0869-US1), now abandoned;

(3) Ser. No. 556,740, filed Nov. 30, 1983, by Wasley (MP0892-US1) now abandoned;

(4) Ser. No. 556,829, filed Dec. 1, 1983, by Wasley (MP0892-US2) now abandoned, which is a continuation-in-part of Ser. No. 556,740;

(5) Ser. No. 618,106, filed Jun. 7, 1984, by Hauptly (MP0920-US1) now abandoned;

(6) Ser. No. 618,109, filed Jun. 7, 1984, by Reeder (MP0923-US1) now abandoned;

(7) Ser. No. 618,108, filed Jun. 7, 1984, by Brooks and Tolles (MP0924-US2) now abandoned, which is a continuation-in-part of Ser. No. 603,485, filed Apr. 24, 1984, by Brooks and Tolles (MP0924-US1), now abandoned;

(8) Ser. No. 603,484, filed Apr. 24, 1984, by Frank and Bonomi (MP0932-US1) now abandoned;

(9) Ser. No. 691,291, filed Jan. 14, 1985, by McCoy and Hauptly (MP1020-US1) now abandoned;

(10) Ser. No. 809,321, filed Dec. 17, 1985, by McCoy and Hauptly (MP1020-US2) now abandoned, which is a continuation-in-part of Ser. No. 691,291;

(11) Ser. No. 744,170, filed Jun. 12, 1985, by Stewart, Lahlouh and Wasley (MP1072-US1) now abandoned;

(12) Ser. No. 787 278, filed Oct. 15, 1985, by Stewart, Lahlouh, Wasley, Hauptly and Welsh (MP1072-US2) now abandoned, which is a continuation-in-part of Ser. No. 744,170; and

(13) Ser. No. 831,758 filed Feb. 20, 1986, by Nyberg and Klingman (MP1094-US1) now abandoned.

The disclosure of each of the pending and abandoned applications referred to above is incorporated herein by reference.

BACKGROUND OF THE INVENTION

Field of the Invention

This invention relates to methods and apparatus for detecting and obtaining information about (particularly locating) changes in variables which take place at one or more locations along an elongate path.

Introduction to the Invention

A number of methods have been used (or proposed for use) to detect changes in variables along an elongate path, e.g. the occurrence of a leak (of water or another liquid or gas), insufficient or excessive pressure, too high or too low a temperature, the presence or absence of light or another form of electromagnetic radiation, or a change in the physical position of a movable member, e.g. a valve in a chemical process plant or a window in a building fitted with a burglar alarm system. Changes of this kind are referred to in this specification by the generic term "event". Such detection methods are for example highly desirable to detect leaks from steam lines into thermal insulation surrounding such lines, leaks from tanks and pipes containing corrosive or noxious chemicals, or leakage or condensation of water under floors or within telecommunication or electrical power systems. Some of these known methods not only signal when the event takes place, but also indicate the location of the event. However, the known methods which indicate the location of the event suffer from serious disadvantages. For example, they make use of time domain reflectometer techniques (and are, therefore, expensive), and/or give unreliable results when used over usefully long elongate paths or under conditions when there may be a substantial and unknown variation along the length of the path of a variable which effects the accuracy of the measurement (especially temperature), and/or make use of electrical conductors whose primary purpose is to carry a current (e.g. a telecommunication signal) under normal operating conditions (and which therefore have resistance and uniformity characteristics consistent with that purpose), and/or cannot be used when the event causes electrical connection between two conductors through a connection which is of high or indeterminate resistance, e.g. an ionically conductive connecting element. Reference may be made for example to U.S. Pat. Nos. 1,084,910, 2,581,213, 3,248,646, 3,384,493, 3,800,216, 3,991,413, 4,278,931 and 4,400,663, U.K. Patents Nos. 1,481,850 and 182,339 and German Offenlegungschriften Nos. 3,001,150.0 and 3,225,742. The disclosures of each of the patents, applications and other publications referred to above are incorporated herein by reference.

SUMMARY OF THE INVENTION

In accordance with the present invention, we have now discovered improved methods and apparatus for monitoring for the occurrence of an event, and for detecting and obtaining information about the event upon its occurrence (i.e. as soon as it occurs or at some time after it has occurred). In the method of the invention, upon occurrence of the event, at least one electrical connection is made between an elongate source member and an elongate locating member of known impedance characteristics, the connection or connections being effective at a first point at which the event takes place (or whose location as defined by some other characteristic of the event). The making of the connection enables the formation of a test circuit which contains the electrical connection(s) and that part of the locating member which lies between the first point and a second point on the locating member whose location is known. A current of known size is then driven through the electrical connection(s) and down the locating member to the second point. The voltage drop between the first and second points is then measured and the location of the first point can then be determined. An important feature of the invention is that the test circuit contains a balancing component which is (a) connected in series with that part of the locating member which lies between the first and second points, and (b) has an impedance which is substantially equal to the difference between (i) the total impedance of the locating member and (ii) the impedance of that part of the locating member between the first and second points. The presence of this balancing component results in a system whose sensitivity is independent of the location of the event. Thus in the absence of the balancing component, the smaller the distance between the first and second points, the lower the impedance of the test circuit, and, as a result, the greater the sensitivity of the system. The system preferably makes use of a locating member having an impedance which is selected to give a desired degree of accuracy in locating the first point, and which preferably does not vary substantially within the temperature range in which the system operates.

When the occurrence of the event causes a single or very short connection to be made between the locating member and the source member, then the "first point" will of course be easily identified, since it is the only connection point. However, when the event results in connection at two or more spaced-apart locations and/or over a finite length of the locating member, the "first point", i.e. the point whose location can be determined from the observed voltage drop, is some intermediate point which can conveniently be referred to as the "electrical center" of the various connections. If there are connections at two or more spaced-apart locations, the "electrical center" may be at a location at which there is no connection between the locating and source members. It is for this reason that the connection to the locating member is sometimes referred herein as being "effective" at the first point. However, it is to be understood that where reference is made herein to the connection being "made" at the first point, this is intended to include situations in which a plurality of electrical connections are made between the locating member and the source member, with the electrical center of the connections being at the first point. In many cases, the first point will be at, or close to, that point at which a connection is made and which is closest to the second point; however, it is important to realize that this is not necessarily the case.

For many uses of this invention, a particularly important advantage is that the information obtained can be independent the impedance of the connection to the locating member, i.e. the information obtained remains the same even if a substantial and unknown change is made in the impedance of the connection. This is the case, for example, when the event is the presence of water or another electrolyte which makes an ionic connection between the source and locating members.

In one aspect, the invention provides a method for monitoring for the occurrence of an event, and for detecting and obtaining information about the event upon its occurrence, which method comprises (1) providing a system
 (a) which comprises a power source, a voltage-measuring device, an elongate electrically conductive locating member and an elongate electrically conductive source member, the locating member comprising a plurality of available connection points and having an impedance $Z_{total}$ between the most widely separated connect ion points, and
 (b) in which, upon occurrence of the event, electrical connection is made between the locating member and the source member; the connection to the locating member being effective at a first point whose location is defined by at least one characteristic of the event;
 the making of the connection enabling the formation of a test circuit which comprises (i) that part of the locating member which lies between the first point and a second point having a known location on the locating member, (ii) the connection, (iii) the power source, and (iv) a balancing component which is connected in series with said part (i) and which has an impedance equal to the difference between $Z_{total}$ and the impedance of said part (i), the power source causing an electrical current of known size to be transmitted between the first and second points on the locating member; and
 the current and the locating member being such that, by measuring the voltage drop between the first and second points, the spatial relationship between the first and second points can be determined;

(2) monitoring the system to determine when a said connection has been made, said test circuit being in existence while said monitoring is taking place if a said connection has been made; and (3) when it is determined that a said connection has been made, using the voltage-measuring device to determine the voltage drop between the first and second points; and (4) obtaining information concerning the event from the measurement made in step (3).

In a preferred embodiment
(a) the system comprises an elongate electrically conductive auxiliary member
(b) the locating, source and auxiliary members follow an elongate path having a near end and a far end,
(c) the second point on the locating member is an the near end of the path,
(d) the auxiliary member is electrically connected to the source member at the far end of the path, and
(e) the locating and source members have substantially the same impedance characteristics
whereby the balancing component (iv) in the test circuit is provided by that part of the source member which lies between the first point and the far end of the path.

Preferably the voltage drop between the first and second points is determined by means of a voltage-measuring device which forms part of a reference circuit, the reference circuit comprising
 (a) the voltage-measuring device,
 (b) that part of the locating member which lies between the first and second points, and
 (c) an elongate electrically conductive return member which (i) is electrically connected to the locating member at the second point and at another point on the locating member whose distance from the second point is at least as great as the distance from the second point to the first point, both distances being measured along the locating member, and (ii) is otherwise insulated from the locating member, the voltage-measuring device having an impedance which is very high by comparison with any unknown part of the impedance of the other components of the reference circuit.

In another aspect, the invention provides apparatus suitable for carrying out the method defined above, in particular apparatus comprising (1) an elongate electrically conductive locating member which comprises a plurality of available connection points, which has an impedance $Z_{total}$ between the most widely separated available connection points, and whose impedance from one end to any of the connection points defines the spatial relationship between that end and that point;

(2) an elongate electrically conductive source member;

(3) an event-sensitive connection means which is present at said plurality of available connection points and which, upon occurrence of an event, at any of said available connection points, permits or effects electrical connection between the locating member and the source member at one or more of the connection points, the connection being effective at a first point on the locating member which is defined by at least one characteristic of the event;

(4) a voltage-measuring device for determining the voltage drop between the first point and a second point which is at one end of the locating member; and (5) a power source which is electrically connected to the second point on the locating member and which, in the absence of an event, is not otherwise connected to the locating member, so that, when occurrence of an event causes an electrical connection to be made between the locating and source members, this enables the formation of a test circuit which comprises (i) that part of the locating member which lies between the first and second points, (ii) the connection, (iii) the power source, and (iv) a component which is connected in series with said part (i) and which has an impedance substantially equal to the difference between $Z_{total}$ and the impedance of said part (i), the power source causing an electrical current of known size to be transmitted between the first and second points on the locating member.

The apparatus preferably also includes an auxiliary member and/or a return member as described above.

Preferably the source and locating members, and the auxiliary and return members (when present) are physically secured together to form a sensor cable. In such a cable at least one, and preferably all, of the members are in a wrapped, e.g. braided, configuration. Such a configuration results in substantial advantages, including in particular:

(a) the ability to produce, from a limited inventory of starting materials, a range of sensor cables of very different properties, in particular of different resolutions (which depends on the impedance per unit length of cable of the locating member) and of different sensitivities (when this depends on the physical separation of the source and locating members) by changes in easily adjusted manufacturing variables, e.g. the pitch of the wrapping, the separation of the wrapped components, and the means used to separate the wrapped components;

(b) the ability to produce a cable having different properties along its length by changes in easily adjusted manufacturing variables, e.g. the pitch of the wrapping;

(c) the ability to incorporate into the cable additional elongate electrical elements which can be used, for example, for continuity testing or ground fault detection;

(d) the ability to incorporate a further locating member, and/or a further source member, so that the cable will detect changes in more than one variable;

(e) the ability easily to manufacture cables in which at least one of the source and location members is a bare wire;

(f) the ability to manufacture a cable having a circular cross-section, so that it is compliant in all planes and is equally sensitive in all planes to the change(s) to be detected; and (g) substantial manufacturing economies by comparison with extrusion processes.

As noted above, the balancing component (iv) results in a system whose sensitivity is independent of the location of the event. Another important advantage is that since the impedance of the connection(s) between the locating and source members is the only variable impedance in the test circuit (or in other circuits which can be created by appropriate switching arrangements), it is possible to determine the impedance of the connection(s). This is useful, for example, in order to determine whether the impedance is changing with time.

It is also possible to create a system in which the Lest circuit will not be maintained if the impedance of the event exceeds a predetermined value.

When this specification refers to the locating member having "a plurality of available connection points", this means that the locating member can have continuous or discrete available connection points.

In making use of the invention, using a controlled current source delivering a "fixed" current in order to detect the presence of electrolytes, we found that false information was sometimes obtained when a very small amount of electrolyte was present, so that the locating and source members were connected to each other through a connection whose resistance was so high that the "controlled current" source was no longer able to supply the expected current because its compliance voltage (i.e. the maximum voltage which the current source can provide) was insufficient to drive the "fixed" current in the test circuit. In one embodiment of this invention, this problem is solved by including in the system one or more components which (a) monitor the current in the test circuit, and
(b) prevent the delivery of information if the current falls below the "fixed" value.

It can also be desirable, when the power source in the test circuit is a controlled current source, to prevent the delivery of information when the impedance of the connection is within some predetermined range (e.g. above some predetermined level), even when part or all of that predetermined range is not such as to cause the current in the test circuit to fall below the "fixed" level. Under these circumstances, the information will be correct, but unwanted, and in accordance with another embodiment of the present invention, the system is modified to include one or more components which (a) monitor the output voltage of the current source (the voltage required to deliver the "fixed" current to a particular test circuit) and
(b) prevent delivery of information if the output voltage is within a predetermined range.

Similarly, when the power source in the test circuit is a constant voltage source, it may be desirable to prevent the delivery of information when the impedance of the connection is within some predetermined range (e.g. above a certain level or below a certain level). Under these circumstances, too, the information will be correct, but unwanted, and in accordance SO with another embodiment of the present invention, the system is modified to include one or more components which (a) monitor the current in the test circuit; and
(b) prevent delivery of information if the current is within a predetermined range.

In one preferred embodiment of this invention, the power source in the test circuit has an output voltage V volts and causes an electrical current I amps of known size to be transmitted between the first and second points on the locating member, and information concerning the event is obtained only when the value of the ratio V/I is within a predetermined range (i.e. above a particular value, or below a particular value, or between two particular values).

Another embodiment of the invention makes use of a reference impedance connected in series with the locating member. When an event takes place, the voltage drop down the locating member, from one end to the location of the event, and the voltage drop across the reference impedance, are determined. A divider provides a ratio between the voltage drops and the location of the event is determined from that ratio. A particular advantage of such modified systems is that variations in the size of the current do not have an adverse effect on the accuracy of the location.

As a result, a power supply, e.g. a current supply, need not be a constant current source and variations in "constant current" do not matter, that is, the output of the power supply need not be monitored or known at all moments of time.

The term divider is used herein to denote any device which obtains from the measurements of the voltage drops the desired information about the event.

The apparatus of the invention preferably also contain a display which is activated by the divider when it provides a ratio between the first and second voltage drops.

In one embodiment of the invention, particularly when the event to be detected is the presence of a hydrocarbon or other organic fluid, the electrical connection of the source and locating members is effected by the swelling of a swellable member which swells when the event occurs. The connection can be effected in a number of different ways. In one type of device, the swellable member is adjacent to a separator which has apertures passing therethrough, and the swelling of the swellable member causes an electrical path to be formed between the conductive members, through the apertures of the separator. In another type of device, the swellable member is a bridging member which, upon occurrence of the event, swells into contact with the source and locating members and bridges them, whereby an electrical path is formed therebetween. In another type of device, the swellable member is part of a device comprising:

i) an elongate support core having a uniform cross-section along its length;
ii) an elongate spacer member;
iii) the locating member;
iv) the source member in the form of a member which is hollow and surrounds the support core, spacer member and first conductive member; and
v) the swellable member;

said spacer member projecting outwardly from the support core a greater distance than the locating member such that in the absence of an event it spaces the source and locating members from each other.

BRIEF DESCRIPTION OF THE DRAWINGS

The invention is illustrated by the accompanying drawing, in which

FIGS. 1 and 5 to 11 are schematic circuit diagrams of systems of the invention, and FIGS. 2 to 4 are graphs showing how the voltage drop between the first and second points on the locating member can vary in different methods of the invention.

DETAILED DESCRIPTION OF THE INVENTION

In the interests of clarity, the following detailed description of the invention includes sections which are chiefly or exclusively concerned with a particular part of the invention. It is to be understood, however, that the relationship between different parts of the invention is of significant importance, and the following detailed description should be read in the light of that understanding. It should also be understood that, where features of the invention are described in the context of particular parts of the invention and/or particular Figures of the drawing, the same description can also be applied to the invention in general and to the other Figures, insofar as the context permits.

1. THE ELECTRICAL CHARACTERISTICS

The basic electrical characteristics of the invention can best be understood by reference to FIG. 1. In FIG. 1, there is an elongate locating member 11, an elongate source member 12, an elongate auxiliary member 13, a voltage-measuring device 14, a power source 15 and an elongate return member 16. The source member is electrically connected, through the auxiliary member and the power source, to the near end of the locating member; in the absence of an event, there is no other electrical connection between the locating member and the source member. Between the source and locating members (but not shown in FIG. 1) is an event-sensitive connection means (this term being used to include a continuous event-sensitive connection means and a plurality of spaced-apart event-sensitive connection means) which becomes conductive at any location at which an event takes place. In FIG. 1, an event has taken place at a first point 1 which lies somewhere on the locating member, but whose location is otherwise unknown. As a result of the event, an electrical connection E has been made between the locating and source members. The power source 15 is connected to the locating member at the near end thereof, designated by the numeral 2, which is the "second point" in the definitions given above of the method and apparatus of the invention. (The second point could be at any point of known location between the end of locating member 11 and the connection point 1, providing that the voltage-measuring device is arranged to measure the voltage drop between the first and second points.) The power source is also connected to the far end of the source member via the auxiliary member 13. Thus the making of the connection at point 1 results in the formation of a test circuit which includes the connection, the locating member between points 1 and 2, the power source and the source member between point 1 and the far end.

The voltage-measuring device is connected to the second point 2 on the locating member and (via the return member 16) to the far end of the locating member. Thus the voltage-measuring device forms part of a reference circuit which comprises the device, the locating member, and the return member.

It will be seen that the location of point 1 can be calculated if the following are known:

(a) the current flowing between points 1 and 2,
(b) the impedance of the components of the reference circuit,
(c) the voltage drop measured by the voltage-measuring device,
(d) the location of point 2, and
(e) the impedance of the locating member between point 2 and each point on the locating member.

The accuracy with which the first point can be located is limited by the ratio of the impedance of the voltage-measuring device to any unknown part of the impedance of the other components of the reference circuit, and in most cases it is convenient to use components such that the ratio of the impedance of the device to the total impedance of the rest of the reference circuit is very high. Accordingly, these ratios should preferably be at least 100, particularly at least 1,000, especially at least 10,000. By contrast, the resistance of the connection between the locating and source members, and the resistance of the other components of the test circuit, do not affect the accuracy of the information obtained.

2. INFORMATION WHICH CAN BE PROVIDED ABOUT AN EVENT

In many cases, the information provided about the event is its location, particularly when the event takes place at (or near) the location of the first point. However, the information provided can be other information; for example when the temperature at a particular location is being monitored, one point on the locating member can be identified when the temperature is in one temperature range and another point can be identified when the temperature is in a different temperature range. As just noted, the location of the event may be at, or close to, the first point on the locating member. However, this is not necessarily so; for example, one or more remote event-detecting stations can be connected, electrically or otherwise, to different points on a central locating member, the locations of the connection points being characteristic of the locations of the event-detecting stations. The method of the invention can provide some, but not necessarily all, the desired information about the event. For example, the method can usefully be employed to determine that a given event (e.g. the opening of a valve) has taken place at one or more of a relatively small number of different locations, out of a relatively large number of possible locations for the event, leaving it to visual inspection or some other form of test (which may be a further and different method of the invention) to determine precisely where the event has taken place.

3. EVENTS WHICH CAN BE DETECTED, AND EVENT-SENSITIVE CONNECTION MEANS FOR DETECTING THEM

The event which is detected in the method of the invention can be an event which is not desired (a fault) or an event which is desired. The event can be the existence of a particular condition or a change in a single variable, e.g. an increase in pressure above a particular value, or a simultaneous or sequential change in two or more variables, e.g. an increase in pressure accompanied by an increase in temperature. The event can be a change in a variable which lasts for only a very short time, or a change in a variable which is maintained for some minimum time. The event can be of any kind which directly or indirectly permits or causes the current to be transmitted between the first point and the second point on the locating member. As noted above, the information obtained is independent of the impedance of the connection. Thus the connection between the locating and source members can be of any kind, for example an electronic connection (which can be of substantially zero impedance or can have substantial impedance), or an ionic connection resulting from the presence of an electrolyte, or an inductive connection. The change which takes place in order to effect the connection between the locating and source conductors is preferably a reversible change. However, the invention is also useful when the change is a permanent one, so that the apparatus must be replaced or repaired before the system is operational again. The system can be arranged so that it signals an event only while the event is taking place or so that it signals that an event has occurred in the past; in the latter case, the system will normally be arranged so that it can be reset.

Examples of events which can be detected include, but are not limited to, the following.

A. The presence of water or another electrolyte which provides an ionic connection between exposed surfaces of the locating and source members, especially when at least part of at least one of these comprises a metal core surrounded by a conductive polymer. In this case, the event-sensitive connection means can be merely a space between the locating and source members, or it can be a connection member on which the electrolyte collects or which absorbs the electrolyte.

B. The existence of a temperature which is below a first temperature $T_1$ or above a second temperature $T_2$. In one apparatus for detecting such a condition, the locating and source members are physically contacted by a connecting member which insulates them from each other at $T_1$ and connects them no each other at $T_2$. For example, at least part of the connecting member can comprise (a) a first material and (b) a second material which is dispersed in the first material and which forms mobile ionic species when the temperature changes from $T_1$ to $T_2$. Thus the first material can be one which changes phase, e.g. melts, when the temperature changes from $T_1$ to $T_2$.

In another apparatus for detecting a temperature change, the locating and source members are separated from each other by a deformable insulating medium, e.g. an insulating medium which is at least in part a fluid, e.g. air, and the apparatus comprises a connecting member which changes shape when the temperature changes from $T_1$ to $T_2$, thus forcing the members into contact, by deforming the insulating medium, or, if the connecting member is itself conductive, by forcing the connecting member through the insulating medium to connect the members. The connecting member can comprise a heat-recoverable polymer or a heat-recoverable memory metal or can comprise a bimetallic strip. The term "memory metal" is used herein to denote one of the metal alloys (in particular various brass alloys and nickel-titanium alloys) which exist in a strong austenitic state above a transformation temperature and in a weak martensitic state below that transformation temperature, and which, if fabricated in a first shape in the austenitic state, can be cooled to the martensitic state and then deformed, will retain the deformed configuration until reheated to the austenitic state, when they will revert (or attempt to revert) towards the original shape. Where a reversible effect is desired, a particular type of memory metal must be employed or the memory metal member can be combined with a conventional spring metal member to produce a connecting member which will connect the locating and source members either when the temperature rises above the transformation temperature or when it falls below the transformation temperature (as more specifically discussed below, in connection with the Figures). For further details of memory metals and devices comprising them, reference may be made for example to U.S. Pat. Nos. 3,174,851, 3,740,839, 3,753,700, 4,036,669, 4,144,104, 4,146,392, 4,166,739 and 4,337,090, the disclosures of which are incorporated herein by reference.

C. A change in the concentration of a particular substance, which may for example be a gas, a liquid or a solid dispersed in a gas or a liquid, the locating and source members being physically contacted by a connecting member which insulates them prior to said change, and which electrically connects them as a result of said change. The electrical connection can for example result from a chemical reaction between the substance and at least part of the connecting member, thus for example releasing a mobile ionic species. Alternatively, the presence of the substance can for example cause at least part of the connecting member to change shape, as for example where the substance causes swelling of a conductive polymer connecting member or where the substance is a solvent for an adhesive or polymeric retaining member which maintains a spring member in a deformed state, or can change the state of an ionization chamber, for example in a smoke detector, or the transmissivity of a photoelectric cell, which in turn will cause a switch to connect the locating and return members.

D. A change from a first pressure $P_1$, to a second pressure, $P_2$, the locating and source members being contacted by a connecting member which insulates them from each other at pressure $P_1$ but permits electrical connection between them at pressure $P_2$. For example, the connecting member can be deformable, e.g. composed of air or other fluid insulating material.

E. A change in the intensity or other characteristic of electromagnetic radiation, the locating and source members being physically contacted by a connecting member which is exposed to said radiation, which insulates them from each other prior to said change and which electrically connects them to each other after said change. Suitable apparatus could for example include a photoelectric cell.

F. A change in the position of a valve, e.g. in a refinery or other chemical process plant, thus changing the position of a switch in a connecting member between the locating and source members.

(4) THE LOCATING, SOURCE AND RETURN MEMBERS

The locating member is an elongate member, this term being used to denote a member having a length which is substantially greater, e.g. at least 100 times greater, often at least 1,000 times greater, sometimes at least 10,000 times greater or even at least 100,000 times greater, than either of its other dimensions.

The source member preferably has the same general configuration and follows the same general path as the locating member. Thus it is preferred that the locating and source members are elongate members which follow the same elongate path, often (but by no means necessarily) parallel to each other.

In many cases, the return member which forms part of the reference circuit also has the same general configuration and follows the same general path as the locating member. This is preferred in one embodiment of the invention in which the source and locating members are elongate and the return member is electrically connected to the locating member at the ends thereof but is otherwise insulated therefrom; on the other hand it is not necessary in this embodiment when the locating and source members follow a path in the form of a loop, so that the return member can be a relatively short member which joins (via the voltage-measuring device) the two ends of the locating member. The return member will usually follow the same general path as the return and locating members in another embodiment in which, when an event occurs, not only is a connection made between the locating and source members, but also an electrical connection of known resistance is made between the return member and the locating member at the first point or at some other point on the locating member which is further away from the second point.

In many cases, it is convenient for one, two or all three of the locating, return and source members to comprise simple conductors which have resistance but no reactance. The locating, return and source members can be the same or different. In order to reduce the input voltage required to provide a controlled current in the test circuit, the source member can be less resistive than the locating member. On the other hand, it is convenient, for providing the essential balancing component (iv), and also for making splices between cables at intermediate points, if the locating and source members to be identical. In order to ensure that the resistance of the return member is not significant in the reference circuit, the return member can be less resistive than the locating member.

The locating member preferably has sufficient impedance to cause a voltage drop which is easily and accurately measured. Preferably, therefore, it has a resistance of at least 0.1 ohm/ft, particularly at least 1 ohm/ft, e.g. 1 to 5 ohm/foot. On the other hand, its resistance should preferably not be too high and is preferably less than $10^4$ ohm/foot, particularly less than $10^2$ ohm/foot, especially less than 20 ohm/foot. A key feature of the present invention is that, under the conditions of operation, the impedance of the locating member is dependent substantially only on the length thereof between the second point and the connection point. This is essential because it is not otherwise possible to calculate the location of the connection point from the change in voltage measured by the voltage-measuring device. The locating member may be of constant cross-section along its length so that its resistance per unit length is constant and the voltage change is directly proportional to the distance between the first and second points. However, this is not essential, providing that the impedance changes in a known fashion along the length of the member, so that the voltage change and the distance can be correlated. The most common variable affecting the resistivity (and, therefore, resistance) of the locating member is temperature. Many materials, and in particular copper and other metals most commonly used for electrical conductors, have a resistivity which changes with temperature to an extent which, although unimportant for many purposes, can result in unacceptable margins of error in locating the first point under conditions in which the temperature can vary substantially and unpredictably along the length of the locating member. It is preferred, therefore, that the locating member should have a temperature coefficient of impedance (usually resistance) which averages less than 0.003, particularly less than 0.0003, especially less than 0.00003, per degree Centigrade over at least one 25° temperature range between −100° C. and +500° C., and preferably over the temperature range 0° to 100° C., especially over the temperature range 0° to 200° C. For a simple metal conductor, the temperature coefficient of impedance is the same as the temperature coefficient of resistivity. The value for copper is about 0.007 per deg C. Metals having lower temperature coefficients of resistivity are well known and include Constantan (also known as Eureka), Manganin and Copel, and others listed for example in the International Critical Tables, published 1929 by McGraw-Hill Book Co., Vol. VI, pages 156-170.

It is of course important that the locating, source and return members should be sufficiently strong, and should be assembled in such a way, that they can withstand the stresses on them during installation and use. For the return member this usually presents no problem, because it can be and preferably is securely enclosed in a conventional polymeric insulating jacket. However, electrical contact is necessary at intermediate points of the locating and source members. This can result in problems, particularly when one or more of the members is a wire of relatively small cross-section. However, we have found that in many applications of the invention, especially those in which the event is the presence of an electrolyte, an excellent combination of desired properties can be obtained through the use of a locating member and/or a source member comprising a metal core and an elongate jacket which electrically surrounds the core and which is composed of a conductive polymer. The term "electrically surrounds" is used herein to mean that all electrical paths to the core (intermediate the ends thereof) pass through the jacket. Normally the conductive polymer will completely surround the core, being applied for example by a melt-extrusion process; however it is also possible to make use of a jacket which has alternate insulating sections and conductive sections. The conductive polymer not only provides physical strength but also prevents corrosion of the metal core.

The term "conductive polymer" is used herein to denote a composition which comprises a polymeric component (e.g. a thermoplastic or an elastomer or a mixture of two or more such polymers) and, dispersed in the polymeric component, a particulate conductive filler (e.g. carbon black, graphite, a metal powder or two or more of these). Conductive polymers are well known and are described, together with a variety of uses for them, in for example U.S. Pat. Nos. 2,952,761, 2,978,665, 3,243,753, 3,351,882, 3,571,777, 3,757,086, 3,793,716, 3,823,217, 3,858,144, 3,861,029, 4,017,715, 4,072,848, 4,117,312, 4,177,446, 4,188,276, 4,237,441, 4,242,573, 4,246,468, 4,250,400, 4,255,698, 4,271,350, 4,272,471, 4,304,987, 4,309,596, 4,309,597, 4,314,230, 4,315,237, 4,317,027, 4,318,881 and 4,330,704: J. Applied Polymer Science 19 813-815 (1975), Klason and Kubat; Polymer Engineering and Science 18, 649-653 (1978), Narkis et al; and commonly assigned U.S. Ser. Nos. 601,424 (Moyer), now abandoned, published as German OLS 2,634,999; 750,149 (Kamath et al), now abandoned, published as German OLS No. 2,755,077; 732,792 (van Konynenburg et al), now abandoned, published as German OLS No. 2,746,602; 751,095 (Toy et al), now abandoned, published as German OLS No. 2,755,076; 798,154 (Horsma et al), now abandoned, published as German OLS No. 2,821,799; 134-354 (Lutz); 141,984 (Gotchef et al), published as European Application No. 38,718; 141,987 (Middleman et al), published as European Application No. 38,715, 141,988 (Fouts et al), also published as European Application No. 38,718, 141,989 (Evans), published as European Application No. 38,713, 141,991 (Fouts et al), published as European Application No. 38,714, 142,053 (Middleman et al), published as European Application No. 38,716, 150,909 (Sopory) and 150,910 (Sopory), published as UK Application No. 2,076,106A, 184,647 (Lutz), 250,491 (Jacobs et al) 273,525 (Walty), 274,010 (Walty et al), 272,854 (Stewart et al), 300,709 (van Konynenburg et al), 369,309 (Midgley et al), and 380,400 (Kamath). The disclosure of each of the patents, publications and applications referred to above is incorporated herein by reference.

The resistivity of conductive polymers usually changes with temperature at a rate well above the preferred temperature coefficient of resistivity set out above, and the PTC conductive polymers often increase in resistivity by a factor of 10 or more over a 100° C. range. Accordingly it is important that in a locating member comprising a conductive polymer jacket, at all temperatures likely to be encountered, e.g. at all temperatures from 0° to 100° C., each longitudinal section of the conductive polymer jacket has a resistance which is at least 100 times, preferably at least 1000 times, the resistance of the core of that longitudinal section. In this way (since the core and the jacket are connected in parallel), the jacket does not make any substantial contribution to the resistance of the elongate conductor, and any change in its resistance with temperature is unimportant.

The second point on the locating member must have a known location, and it is normally a fixed point. When the system is designed to detect different types of events occurring independently, the second point is preferably the same fixed point for detection of the different events. In the case of an elongate locating member, the second point will normally be at one end or the other of the locating member. However, the invention includes, for example, the simultaneous or sequential use of a plurality of second points to determine the locations of a plurality of first points when a number of different events having identified a number of first points.

(5) THE POWER SUPPLY

The current which is transmitted between the first and second points must be of known size, and is preferably supplied by a controlled current source, e.g. a galvanostat; however, a controlled voltage source can be used providing that a current-measuring device is included in the apparatus so that the location of the first point can be calculated. The current may be a direct current or an alternating current of regular sinusoidal or other form. The current which flows between the first and second points is preferably in the range of 0.05 to 100 milliamps, particularly 0,1 to 10 milliamps, e.g. 0.5 to 3 milliamps. The controlled current source is preferably a fixed current source or a current source which can be adjusted to a desired and known value, for example to obtain improved accuracy in locating a fault which was detected at a lower current level. However, it is also possible to use a fixed voltage source, in combination with a current-measuring device which measures the current flowing between the first and second points. As noted above, the current can be known indirectly through measurement (including comparison) of the voltage drop over a reference resistor. The power source is preferably connected to the locating member at the second point at all times and, in the absence of an event, may be otherwise insulated from the locating member.

(6) THE VOLTAGE-MEASURING DEVICE

The voltage-measuring device can be of any kind, and suitable devices are well known to those skilled in the art. Preferably the voltage-measuring device is a voltmeter which has a resistance of at least 10,000 ohms, preferably at least 1 megohm, especially at least 10 megohms.

(7) VOLTAGE DROP VS. DISTANCE

The relationship between the voltage drop measured by the voltage-measuring device and the distance between the first and second points will depend on the way in which the apparatus is designed. When connection can be made to the locating member at any point along its length, and the locating member is of uniform impedance along its length, then the relationship will be a straight line of uniform slope, as illustrated in FIG. 2. When the event-sensitive connection means is discontinuous, so that connection to the locating member is possible only at spaced-apart points, then the relationship will be a series of steps as shown in FIG. 3. When the locating member is divided into locating and connection zones and can be contacted at any point within a locating zone, then the relationship is as shown in FIG. 4.

(8) WRAPPED SENSOR CABLES

As noted above, at least one of the elongate connection means preferably has a wrapped configuration. For example, the source and locating members can be wrapped around the return member, which is preferably an insulated wire. The wrapping is preferably a spiral wrap of constant pitch, but other types of wrap can be used, and the pitch can vary along the length of the cable. Wrapping can for example be effected by means of a braiding machine.

When more than one of the elongate connection means has a wrapped configuration, the wrapped connection means are preferably parallel to each other, i.e. are wrapped in the same way and at the same pitch; they can be spaced apart from each other by a jacket composed of an insulating material (which may be apertured to permit an electrolyte to contact the connection means) on one or both of the connection means and/or by an insulating spacer which is wrapped at the same time. In this embodiment, at least one of the first and second connection means is preferably a metal wire having a coating of a conductive polymer thereon. Alternatively, especially when the cable is to be used in an environment which would dissolve or damage, or would be damaged by, a conductive polymer coating, both connection means can be bare wires; such a cable is useful, for example, for the detection of water or another electrolyte in a non-conductive organic solvent such as kerosene or another hydrocarbon, especially to detect the ingress of sea water into a "streamer", i.e. a cable drawn behind a boat and containing, immersed in a non-conductive fluid, a plurality of sonar detection devices.

Alternatively, the wrapped connection means can have different wrapped configurations so that they cross at spaced-apart locations. This can be achieved by wrapping one clockwise and the other anti-clockwise, at the same or different pitches, or by wrapping both in the same direction at different pitches. In this alternative, a preferred embodiment employs first and second connection means which are separated from each other at crossing points by a separator which is an electrical insulator when the variable is in the first state and which effects or permits electrical connection between the first and second connection means when the variable is in the second state; thus the separator (which can be in the form of a jacket on one or both of the first and second connection means) can be composed of a material which becomes conductive, or which softens and flows to allow direct contact between first and second connection means which have been wrapped so that they are pressed into contact.

As briefly noted above, the new cable can comprise one or more locating members and one or more source members, with these, and the means used to keep the source and locating members insulated under normal conditions, being chosen so that the cable will detect changes in more than one variable. In addition, the cable can comprise additional elongate members which may be present simply to provide additional strength or which can be electrically conductive so that they can be used as part of a conventional system for detecting changes, e.g. for continuity testing and ground fault detection.

When the cable includes an auxiliary member and/or other elongate electrical connection means in addition to the source, locating and return members, this additional means preferably also has a wrapped configuration, which may be parallel to one or more of the source, locating and return members or can have an opposite hand or different pitch so that it crosses one or more of the source, locating and return members at spaced apart points.

It is important that the impedance of the locating member should, under the conditions of the method, change in a known way along the length of the cable. To ensure that variations in ambient temperature do not lead to unacceptable margins of error in the location of the change of the variable from the first to the second state, it is preferred that the locating member has a temperature coefficient of impedance which is less than 0.003 per degree Centigrade over at least one 25° C. temperature range between −100° C. and +500° C., and preferably over the temperature range 0° to 100° C.

The cable can be provided with an overbraid of insulating material if desired.

(9) BALANCING COMPONENTS

A number of systems containing balancing components are shown in FIGS. 1 and 5 to 10.

FIG. 1 shows an elongate locating member 11 which has a constant resistance along its length and an impedance $Z_{total}$ between the ends thereof and adjacent elongate source member 12 which is substantially identical to locating member 11. Elongate auxiliary member 13 connects the second (or far) end of the source member 12 to a constant current source 15 and thence to the first (or near) end of the locating member. An elongate return member 16 connects the near and far ends of the locating member, through a high impedance voltmeter 14. An event has occurred, creating connection E at point (1) on the locating member. The voltmeter 14 measures the voltage drop down the locating member between connection point (1) and the second point, which is the near end (2). The section of the source member 12 which lies between the connection E and the far end of the source member provides a balancing component which is connected in series with that part of the locating member which lies between the near end and the connection E and which has an impedance equal to the difference between $Z_{total}$ and the impedance of that part. The test circuit created by the connection E has an impedance which is fixed except for the impedance of connection E, and it is, therefore, possible to select precisely the limits of the impedance of the connection E which will cause the system to signal that an event has taken place.

FIG. 5 is similar to FIG. 1, but the fixed current source is replaced by a fixed voltage source 151 and an ammeter 152. Calculation of the location of the point (1) thus involves knowledge of the current through the ammeter. The current measured by the ammeter 152 also provides a means of measuring the resistance of the connection between the source and locating members.

FIG. 6 is somewhat similar to FIG. 1, but incorporates the following changes:
  (a) the locating member 11 comprises a plurality of resistors 111, which can have the same or different resistances $R_1$ to $R_m$, and a plurality of low resistance intermediate components 112;
  (b) the source member 12 comprises a plurality of resistors 121 which have resistances $R_1$ to $R_m$ which are respectively equal to the corresponding resistors 111 in the locating member, and a plurality of low resistance intermediate components 122;
  (c) the source and locating members each comprise a plurality of spaced-apart available connection points which are provided by a plurality of event-sensitive connection means, each comprising a switch S and a resistor in series therewith, the resistors having resistances $R_A$ to $R_N$ which can be the same or different;
  (d) a reference resistor $R_f$ is connected in series with the locating member, and the voltage drop over the reference resistor is measured by a voltmeter 141.

Thus in FIG. 6, the balancing component is provided by the resistors 121 of the source member which lie between (i) the Switch S which is closed by an event and (ii) the far end of the source member, resulting in a test circuit in which the only variable is the resistor ($R_A$ to $R_N$) which is in series with the closed switch.

FIG. 6 also illustrates novel modules which can be used in the present invention. Thus the two $R_m$ resistors and the switch S between them can form part of a first module; the two $R_2$ resistors and the switch S and resistors $R_8$ between them can form part of a second module; the two $R_3$ resistors and the switch S and resistor $R_c$ between them can form part of a third module; and so on. In the first module, the $R_1$ resistor 111 is the first impedant component, and it is connected, by means of a low impedance conductor, to the incoming and outgoing portions of the locating member 11. Similarly the $R_m$ resistor 121 is the second impedant component, and it is connected, by means of a low impedance conductor, the incoming and outgoing portions of the source member 12. The switch S is an event-sensitive connection means which, upon occurrence of an event, connects the two low impedance conductors.

FIG. 7 is the same as FIG. 1 except that it also includes a second voltmeter 19 which measures the output voltage of the power source. The impedance of the connection E can be calculated from the output voltage (so long as the power source is delivering the desired "fixed" current).

FIG. 8 is somewhat similar to FIG. 1, but incorporates a switch 161 such that the return member can be connected as shown (the system then being precisely as shown in FIG. 1) or can be disconnected from the near end of the locating member and connected to the near end of the source member. In the latter configuration, the voltage measured by the voltmeter is a measure of the impedance of the connection E.

FIG. 9 shows an alternative arrangement which does not require the use of an auxiliary member, but instead makes the return member part of the test circuit, the second point then being at the far end of the system. In FIG. 9, the balancing component is the section of the source member 12 which lies between the connection E and the near end of the source member.

FIG. 10 is somewhat similar to FIG. 1, but incorporates a second voltmeter 20 which is placed so that it measures the voltage drop across the connection E, so that the impedance of the connection can then be calculated.

As indicated by FIGS. 1 to 10, each of the source and locating members can each have substantially the same impedance per unit length throughout its length, or each can comprise
  (a) a plurality of spaced-apart, discrete impedant components, each of which has substantial impedance, and
  (b) a plurality of elongate intermediate members, each of which physically separates and electrically connects a pair of impedant components;
the available connection points lying between the impedant components.

An important feature of this invention is the use of a balancing component which, in the test circuit, (a) is connected in series with that part of the location member between the first and second points and (b) has an impedance substantially equal to the difference between the total impedance of the locating member and the impedance of the locating member between the first and second points. The impedance of the balancing component is preferably exactly equal to said difference, and this can be easily achieved by the measures described above. However, similar but less marked improvement can be obtained if the impedances are not exactly the same. Accordingly the term "substantially equal" is used herein to mean that the impedances generally differ by not more than 25%, preferably not more than 10% particularly not more than 1% (based on the lower of the two impedances).

(10) MEASURING THE IMPEDANCE OF THE CONNECTION

The impedance of the connection between the locating and source members can be measured in a number of different ways. In one method, as shown for example in FIG. 5, the power source is a fixed and known voltage source and the impedance is calculated from the current in the circuit. In another method, as shown for example in FIG. 7, the power source is a fixed and known current source and the output voltage of the power source is measured. In both cases, of course, allowance must be made for the (fixed) impedance of the remainder of the circuit.

In another method, as shown for example in FIG. 8, the power source is a fixed and known current source, and the method includes, after step (3), (4) disconnecting the voltage-measuring device and the first end of the return member from the first end of the locating member;

(5) connecting the first end of the return member to the first end of the source member, via the voltage-measuring device; and (6) determining the impedance of the connection between the locating and source members from the voltage measured by the voltage-measuring device.

In another method, as shown for example in FIG. 9, the system incorporates a second voltmeter which measures the voltage drop across the connection between the locating and source members.

(11) OBTAINING INFORMATION ONLY IN CERTAIN V/I RANGES

When the system is arranged so that information about the event is obtained only when V/I falls within a particular range, that range can easily be changed (for example so that leaks of different minimum sizes are signaled). When using a fixed current source, sensitivity can be changed by changing the compliance voltage of the source, and/or by including a known impedance in the test circuit, and/or by changing the preselected range of output voltages. When using a fixed voltage source, the size of the voltage can be changed, and/or a known impedance can be included in the test circuit, and/or the preselected current value can be changed.

(12) USE OF A REFERENCE RESISTOR

The use of a reference resistor in the test circuit provides the advantage that one does not need to know the size of the current, be it constant or varying. This is particularly useful when a very low current is used, as for example in a very long system which is powered at low voltages, e.g. not more than 24 volts, preferably below 10 volts, so that the system is "inherently safe". Even a "fixed current" source can vary by up to 4% when its value is below 12 milliamps, e.g. 1 to 250 microamps. Preferably, the systems comprises two voltage measuring devices, one measuring the first voltage drop ($V_1$) across the reference impedance, the other measuring the second voltage drop ($V_2$) down the locating member. Alternatively, a single voltage measuring device can be used together with a switch means, to measure sequentially the first and second voltage drops. The switching speed should be faster than any current size variations, so that $V_1$ and $V_2$ are measured at the same current. This embodiment preferably makes use of a divider for providing a ratio between $V_1$ and $V_2$, and preferably also a display, preferably digital, for displaying the ratio obtained. Conventional dividers, switching means and displays can be used for this purpose.

By changing the size of the reference resistor, it is easy to adjust the apparatus for changes in one or more of the following variables:

(1) the length of the locating member;

(2) the units, e.g. metric or Roman, in which the distance to the first point is displayed;

(3) the voltmeters employed and their various scale factors, bearing in mind that full scale deflection of the meter preferably corresponds to the full length of the locating member.

It is important that the reference impedance has a known, fixed value under the conditions of operation. Accordingly, the reference impedance preferably has a temperature coefficient of impedance which averages less than 0.003 per degree C. over the temperature range 0° to 100° C. The reference impedance preferably has resistance and no reactance, with typical values shown in Table I.

TABLE I

| Nominal System Length (ft.) | Reference Resistance (ohms) |
| --- | --- |
| 2,000 | 4k |
| 20,000 | 40k |
| 200,000 | 400k |

A particular value of the reference resistance is selected with an eye to the variables noted above. For example, different lengths of the locating member are accommodated by selecting a reference resistance so that it is preferably 0.01 to 100, especially 0.1 to 10, particularly 0.5 to 2 times the resistance of the full length of the locating member. The system can include two or more reference impedances each of known impedance, and switching means for selecting one or more of the reference impedances so that, when the system is in use, a reference impedance of the desired size is provided.

(13) DEVICES CONTAINING SWELLABLE MEMBERS

As noted above, the systems of the invention can make use of devices containing swellable members which swell upon occurrence of an event. For a more detailed description of such devices, reference should be made to the parent U.S. Pat. No. 5,015,958, incorporated herein by reference.

We claim:

1. A method for monitoring for the occurrence of an event, and for detecting and obtaining information about the event upon its occurrence, which method comprises (1) providing a system (a) which comprises a power source, a voltage-measuring device, an elongate electrically conductive locating member and an elongate electrically conductive source member, the locating member comprising a plurality of available connection points and having an impedance $Z_{total}$ between the most widely separated available connection points, and (b) in which, upon occurrence of the event, electrical connection is made between the locating member and the source member;

the connection to the locating member being effective at a first point whose location is defined by at least one characteristic of the event;

the making of the connection enabling the formation of a test circuit which comprises (i) that part of the locating member which lies between the first point and a second point having a known location on the locating member, (ii) the connection, (iii) the power source, and (iv) a balancing component which is connected in series with said part (i) and which has an impedance substantially equal to the difference between $Z_{total}$ and the impedance of said part (i), the power source causing an electrical current of known size to be transmitted between the first and second points on the locating member; and the current and the locating member being such that, by measuring the voltage drop between the first and second points, the spatial relationship between the first and second points can be determined;

(2) monitoring the system to determine when a said connection has been made, said test circuit being in existence while said monitoring is taking place if a said connection has been made; and (3) when it is determined that a said connection has been made, using the voltage-measuring device to determine the voltage drop between the first and second points; and (4) obtaining information concerning the event from the measurement made in step (3).

2. A method according to claim 1 wherein the system includes a reference impedance which has a known impedance and which forms part of the test circuit and wherein the size of the electrical current transmitted between the first and second points on the locating member has a known relationship with the current through the reference electrode; and wherein the currents the reference impedance and the locating member are such that, by obtaining a ratio between a first voltage drop across the reference impedance and a second voltage drop between the first and second points on the locating member, the spatial relationship between the first and second points can be determined.

3. A method according to claim 1 wherein the system comprises a swellable member which swells upon occurrence of the event, and which has at least one of the following characteristics (a) on swelling it causes an electrical path to be formed between the locating member and the source member through the apertures of an apertured separator, and (b) it is a conductive, bridging member which, upon occurrence of the event, swells into contact with the locating member and the source member and bridges the members, whereby an electrical connection is made between the members.

4. A method according to claim 3 wherein the locating member, the source member and the swellable member are part of a device which comprises i) an elongate support core, ii) the locating and source members helically wrapped around the core, iii) a separator in the form of a braid surrounding the locating and source members, iv) the swellable member in the form of a hollow swellable member which comprises a conductive polymer and which surrounds the the separator braid, and v) a restraining braid surrounding the conductive polymer, and wherein, upon occurrence of an event, the swellable member swells through the apertures of the separator braid, and contacts and bridges locating and source members and makes an electrical connection between them.

5. A method according to claim 3 wherein the locating member, the source member and the swellable member are part of a device which comprises an elongate support core having a uniform cross-section along its length;

ii) a spacer member;

iii) the locating member;

iv) the source member in the form of a member which is hollow and surrounds the support core, spacer member and locating member; and (v) the swellable member;

said spacer member projecting outwardly from the support core a greater distance than the locating member such that in the absence of an event it spaces the source and locating members from each other.

6. A method according to claim 1 wherein the source member and the locating member are identical.

7. A method according to claim 1 wherein the locating member (a) has a temperature coefficient of impedance which averages less than 0.003 per degree over the temperature range 0° to 100° C. and (b) comprises an elongate metal core which is physically and electrically surrounded by a jacket of a composition which comprises a polymeric component and, dispersed in the polymeric component, a sufficient amount of carbon black to render the composition conductive at ambient temperatures.

8. A method according to claim 1 wherein (a) the system comprises an elongate electrically conductive auxiliary member, (b) the locating, source and auxiliary members follow an elongate path having a near end and a far end, (c) the second point on the locating member is at the near end of the path, (d) the auxiliary member is electrically connected to the source member at the far end of the path, and (e) the locating and source members have substantially the same impedance characteristics.

whereby the balancing component (iv) in the test circuit is provided by that part of the source member which lies between the first point and the far end of the hath.

9. A method according to claim I wherein (1) the power source in the test circuit has an output voltage V volts and causes an electrical current I amps of known size to be transmitted between the first and second points on the locating member; and (2) information concerning the event is obtained only when the value of the ratio V/I is within a predetermined range.

10. Apparatus for detecting an event which comprises (1) an elongate electrically conductive locating member which comprises a plurality of available connection points which has an impedance $Z_{total}$ between the most widely separated available connection points, and whose impedance from one end to any of the connection points defines the spatial relationship between that end and that connection point;

(2) an elongate electrically conductive source member;

(3) an event-sensitive connection means which is present at said plurality of available connection points and which, upon occurrence of an event at any of said available connection points permits or effects electrical connection between the locating member and the source member at one or more of the connection points, the connection being effective at a first point on the locating member which is defined by at least one characteristic of the event;

(4) a voltage-measuring device for determining the voltage drop between the first point and a second point which is at one end of the, locating member; and (5) a power source which is electrically connected to the second point on the locating member and, in the absence of an event, is not otherwise connected to the locating member, so that, when occurrence of an event causes an electrical connection to be made between the locating and source members, this enables the formation of a test circuit which comprises (i) that part of the locating member which lies between the first and second points, (ii) the connection, (iii) the power source, and (iv) a component which is connected in series with said part (i) and which has an impedance substantially equal to the difference between $Z_{total}$ and the impedance of said part (i), the power source causing an electrical current of known size to be transmitted between the first and second points on the locating member.

11. Apparatus according to claim 10 wherein the power source is a controlled current source.

12. Apparatus according to claim 10 for detecting and locating, along a longitudinally extending path having a near end and a far end, a change in an ambient condition from a first state to a second state, in which apparatus
(a) the source member lies along said path and has a near end at the near end of the path and a far end at the far end of the path;
the locating member
(i) lies along said path and has a near end at the near end of the path and a far end at the far end of the path, the near end of the locating member being electrically connected to the near end of the source member
(ii) is electrically insulated from the source member at all points along the path when said ambient condition is in the first state at all points along the path,
(iii) when said ambient condition changes from the first state to the second state at at least one point along the path, becomes electrically connected to the source member at a connection point at which said ambient condition has changed from the first state to the second state, thereby creating a test circuit which includes part of the source member and part of the locating member and
(iv) has an impedance from the near end to each point thereon which is characteristic of its length from the near end to that point;
(c) the power Source is a controlled current source which forms part of the test circuit created when said ambient condition changes from the first state to the second state;
and which apparatus further comprises
(d) an elongate electrically conductive return member which has a near end at the near end of the path and a far end at the far end of the path, which is electrically insulated from the source member and the locating member between its near end and its far end when said ambient condition is in its first state and when it is in its second state, and which connects the near end and the far end of the locating member thus forming a reference circuit which contains the
voltage-measuring device said voltage-measuring device having a very high input impedance by comparison with the other components of the reference circuit;
the source member, the locating member, and the return member being physically secured together and at least one of the first, second and third connection means having a wrapped configuration;
whereby it is possible to monitor the voltage-measuring device, and when the voltage measured by the voltage-measuring device changes, to measure the change in the voltage and to calculate therefrom the distance between the near end of the locating and the connection point.

13. Apparatus according to claim 10 wherein the locating member and the source member are wrapped parallel to each other around an insulating core.

* * * * *

UNITED STATES PATENT AND TRADEMARK OFFICE
CERTIFICATE OF CORRECTION

PATENT NO. : 5,382,909

INVENTOR(S) : Masia et al.

DATED : January 17, 1995

It is certified that error appears in the above-identified patent and that said Letters Patent is hereby corrected as shown below:

Drawing Sheet 4, delete Figure 11.
Column 4, line 1, replace "connect ion" by --connection--.
Column 4, line 5, after "member;" begin a new line with "the".
Column 4, line 42, replace "an" by --at--.
Column 6, line 28, replace "Lest" by --test--.
Column 7, line 7, delete "so".
Column 8, line 13, replace "5 to 11" by --5 to 10--.
Column 12, line 42, replace "to be" by --are--.
Column 14, line 13, replace "(Gotchef et al)" by --(Gotcher et al)--.
Column 14, line 57, replace "having" by --have--.
Column 15, line 2, replace "0,1" by --0.1--.

UNITED STATES PATENT AND TRADEMARK OFFICE
CERTIFICATE OF CORRECTION

PATENT NO. : 5,382,909

DATED : Masia et al.

INVENTOR(S) : January 17, 1995

It is certified that error appears in the above-indentified patent and that said Letters Patent is hereby corrected as shown below:

Column 17, line 61, replace "$R_m$" by -- $R_1$ --.
Column 18, line 3, replace "$R_m$" by -- $R_1$ --.
Column 19, line 52, replace "systems" by --system--.
Col. 21, Claim 2, line 4, replace "circuit" by --circuit,--
Col. 21, Claim 2, line 10, replace "currents" by --currents,--.
Col. 21, Claim 4, line 17, insert --the-- after "bridges".
Col. 22, Claim 5, line 4, insert --i)-- before "an".
Col. 22, Claim 8, line 11, replace "characteristics." by --characteristics,--.
Col. 22, Claim 8, line 14, replace "hath" by --path--.
Col. 22, Claim 10, line 5, replace "points" by --points,--.
Col. 22, Claim 10, line 16, replace "points" by --points,--.
Col. 22, Claim 10, line 24, replace "the," by --the--.
Col. 23, Claim 12, line 8, insert --(b)-- before "the locating member".

UNITED STATES PATENT AND TRADEMARK OFFICE
CERTIFICATE OF CORRECTION

PATENT NO. : 5,382,909

DATED : Masia et al.

INVENTOR(S) : January 17, 1995

It is certified that error appears in the above-indentified patent and that said Letters Patent is hereby corrected as shown below:

Col. 23, Claim 12, line 30, replace "Source" by --source--.
Col. 24, Claim 12, line 45, replace "device" by --device,--.
Col. 24, Claim 12, line 57, insert --member-- after "locating".

Signed and Sealed this

Nineteenth Day of March, 1996

BRUCE LEHMAN

*Attest:*

*Attesting Officer*     *Commissioner of Patents and Trademarks*